(12) United States Patent
Frémy et al.

(10) Patent No.: US 11,608,315 B2
(45) Date of Patent: Mar. 21, 2023

(54) PROCESS FOR THE PREPARATION OF METHYL MERCAPTAN

(71) Applicants: Arkema France, Colombes (FR); Université Lille 1—Sciences et Technologies, Villeneuve d'Ascq (FR); Centre National De La Recherche Scientifique—CNRS, Paris (FR)

(72) Inventors: Georges Frémy, Sauveterre de Bearn (FR); Hélori Salembier, Pau (FR); Carole Lamonier, Armentieres (FR); Pascal Blanchard, Lens (FR)

(73) Assignees: Arkema France, Colombes (FR); Universite Lille 1-Sciences et Technologies, Villeneuve d'Ascq (FR); Centre National de la Recherche Scientifique (CNRS), Paris (FR)

( * ) Notice: Subject to any disclaimer, the term of this patent is extended or adjusted under 35 U.S.C. 154(b) by 358 days.

(21) Appl. No.: 16/956,201

(22) PCT Filed: Dec. 20, 2018

(86) PCT No.: PCT/EP2018/086086
§ 371 (c)(1),
(2) Date: Jun. 19, 2020

(87) PCT Pub. No.: WO2019/122072
PCT Pub. Date: Jun. 27, 2019

(65) Prior Publication Data
US 2020/0331852 A1    Oct. 22, 2020

(30) Foreign Application Priority Data
Dec. 22, 2017   (FR) ..................................... 1763023

(51) Int. Cl.
| | | |
|---|---|---|
| *C07C 319/06* | (2006.01) | |
| *C01B 32/77* | (2017.01) | |
| *B01J 21/06* | (2006.01) | |
| *B01J 23/28* | (2006.01) | |
| *B01J 35/10* | (2006.01) | |
| *C07C 319/02* | (2006.01) | |
| *C07C 321/04* | (2006.01) | |
| *C01B 32/70* | (2017.01) | |
| *C07C 319/28* | (2006.01) | |
| *C07C 319/14* | (2006.01) | |

(52) U.S. Cl.
CPC .......... *C07C 319/06* (2013.01); *B01J 21/066* (2013.01); *B01J 23/28* (2013.01); *B01J 35/1014* (2013.01); *C01B 32/70* (2017.08); *C01B 32/77* (2017.08); *C07C 319/02* (2013.01); *C07C 319/14* (2013.01); *C07C 319/28* (2013.01); *C07C 321/04* (2013.01)

(58) Field of Classification Search
None
See application file for complete search history.

(56) References Cited

U.S. PATENT DOCUMENTS

| | | | |
|---|---|---|---|
| 4,665,242 A | 5/1987 | Boulinguiez et al. | |
| 2007/0213564 A1 | 9/2007 | Yang et al. | |
| 2008/0262270 A1 | 10/2008 | Barth et al. | |
| 2010/0094059 A1 | 4/2010 | Yang et al. | |
| 2010/0286448 A1 | 11/2010 | Yang et al. | |
| 2011/0015443 A1* | 1/2011 | Barth | C07C 319/02 |
| | | | 568/70 |

FOREIGN PATENT DOCUMENTS

| | | |
|---|---|---|
| EP | 0171312 A1 | 2/1986 |
| WO | 2005040082 A2 | 5/2005 |

OTHER PUBLICATIONS

International Search Report and Written Opinion for International Application No. PCT/EP2018/086086, dated Mar. 29, 2019, 7 pages.

* cited by examiner

*Primary Examiner* — Philip Y Louie
(74) *Attorney, Agent, or Firm* — RatnerPrestia

(57) ABSTRACT

The invention relates to a process for preparing methyl mercaptan from a mixture of carbon oxide, hydrogen sulfide and hydrogen, in the presence of a catalyst based on molybdenum and potassium supported on zirconia, said catalyst not comprising any promoter.

8 Claims, No Drawings

PROCESS FOR THE PREPARATION OF METHYL MERCAPTAN

CROSS-REFERENCE TO RELATED APPLICATIONS

This is the national phase of International Application No. PCT/EP2018/086086, filed 20 Dec. 2018, which claims priority to French Application No. 1763023, filed 22 Dec. 2017. The disclosure of each of these applications is incorporated herein by reference in its entirety for all purposes.

The present invention relates to a process for preparing methyl mercaptan from carbon oxide, hydrogen sulphide and hydrogen, said process implementing a specific molybdenum- and potassium-based catalyst.

Methyl mercaptan is of great interest to industries, in particular as a raw material for synthesising methionine, an essential amino acid widely used in animal feeds. Methyl mercaptan is also a raw material for numerous other molecules, in particular dimethyl disulphide (DMDS), a sulphiding additive for hydrotreating catalysts for petroleum cuts, among other applications.

Methyl mercaptan is commonly produced in high tonnages on an industrial scale from methanol and $H_2S$, but it can be economically of interest to produce methyl mercaptan directly from carbon monoxide, hydrogen and hydrogen sulphide according to the following reaction:

$$CO + 2H_2 + H_2S \rightarrow CH_3SH + H_2O \qquad (1)$$

The main by-product of this reaction is carbon dioxide ($CO_2$). More specifically, carbonyl sulphide (COS) is considered to be the reaction intermediate producing methyl mercaptan after hydrogenation according to the following reactions:

$$CO + H_2S \rightarrow COS + H_2 \qquad (2)$$

$$COS + 3H_2 \rightarrow CH_3SH + H_2O \qquad (3)$$

The $CO_2$ is the result of a plurality of parasitic reactions such as:

$$CO + H_2O \rightarrow CO_2 + H_2 \qquad (4)$$

$$COS + H_2O \rightarrow CO_2 + H_2S \qquad (5)$$

$$2COS \rightarrow CO_2 + CS_2 \qquad (6)$$

These parasitic reactions, which consume the main raw material, carbon monoxide, and the reaction intermediate, carbonyl sulphide, are caused by the presence of water co-produced during the synthesis of methyl mercaptan.

As described in the European patent application No. 0171312 and in the U.S. patent application No. 2008/262270, carbon dioxide can potentially be recycled to produce methyl mercaptan according to the following reaction:

$$CO_2 + 3H_2 + H_2S \rightarrow CH_3SH + 2H_2O \qquad (7)$$

However, this reaction is known to be slower than that using carbon monoxide. There is thus an interest in keeping carbon dioxide production as low as possible during the synthesis of methyl mercaptan.

Thus, the highest yield capacities for methyl mercaptan are expected using the syngas approach according to reaction (1), i.e. from carbon monoxide, hydrogen and hydrogen sulphide.

The U.S. patent application No. 20070213564 describes a continuous process for the manufacture of methyl mercaptan using carbon monoxide, hydrogen and hydrogen sulphide, said reaction being catalysed by a silica-supported $K_2MoO_4$-based catalyst family. According to this process, 70% of the carbon monoxide can be converted with selectivities to methyl mercaptan, carbon dioxide and carbonyl sulphide respectively equal to 49%, 43% and 8%.

The international patent application No. WO2005/040082 describes a plurality of catalysts and in particular a catalyst comprising a Mo—O—K-based active component, an active promoter and optionally a support. The catalysts used as examples have differing chemical natures such as $K_2MoO_4$/$Fe_2O_3$/NiO or even $K_2MoO_4$/CoO/$CeO_2$/$SiO_2$, each supported on silica. The $CO_2$/MeSH selectivity ratio is 0.88.

The U.S. patent application No. 20100094059 cites a $TeO_2$/$K_2MoO_4$-based catalyst family supported on a porous support selected from $SiO_2$, $Al_2O_3$, $TiO_2$, $Al_2O_3$—$SiO_2$, $ZrO_2$, zeolites, carbonaceous materials, and a promoter exclusively characterised by tellurium oxide ($TeO_2$). It is shown that the carbon monoxide conversion is 59% for a selectivity to methyl mercaptan equal to 55%.

The U.S. patent application No. 20100286448 discloses another family of catalysts formed by a porous support such as $SiO_2$, $TiO_2$, silico-aluminas, zeolites and carbon nanotubes, on which a metal has been electrolytically deposited. $K_2MoO_4$, in addition to another metal oxide acting as a promoter, are then impregnated onto this support. This catalyst produces a conversion comprised between 65% and 66% of the carbon monoxide and a methyl mercaptan yield capacity comprised between 46% and 47%. No data is specified as regards the procedural conditions and the yield capacity of the methyl mercaptan.

The teachings of these documents show that the association of catalysts of a specific structure, of promoters and of supports, each being carefully selected, procures improved selectivities and yields compared to the known processes, while being a process that is carried out in the most cost-effective manner possible.

Despite all of these research works, there remains a need for a catalyst that is easy to prepare and that results in very good selectivities. One of the purposes of the present invention is to show that, thanks to a specific catalyst, the formulation whereof is simpler than that known in the prior art, improved CO conversion results and an improved selectivity and improved yield capacity for methyl mercaptan can be obtained during the synthesis thereof from syngas comprising CO, $H_2$ and $H_2S$.

Thus, the present invention relates to a perfecting of the production of methyl mercaptan ("$CH_3SH$" or more simply "MeSH") from gaseous mixtures enclosing at least one carbon oxide, hydrogen and hydrogen sulphide.

It has now been discovered in a surprising manner that this perfecting can be obtained thanks to the catalyst according to the invention, which is a zirconia-supported molybdenum- and potassium-based catalyst.

The catalyst according to the invention is easier to prepare, in particular since the presence of a promoter is not essential. Moreover, the catalyst according to the invention is also less expensive than those known in the prior art. Finally, the catalyst according to the invention results in an improved conversion of carbon oxide, in particular of carbon monoxide, and an improved selectivity to methyl mercaptan.

According to one preferred embodiment, the catalyst according to the invention is a zirconia-supported molybdenum- and potassium-based catalyst that does not comprise a promoter.

According to one embodiment, the catalyst according to the invention comprises zirconia-supported potassium and molybdenum oxides, and does not comprise a promoter.

According to another embodiment, the catalyst according to the invention is constituted by zirconia-supported potassium and molybdenum oxides.

Thus, according to a first object, the present invention relates to a process for preparing methyl mercaptan, said process comprising at least the following steps:
a) a carbon oxide, hydrogen sulphide ($H_2S$) and hydrogen ($H_2$) undergo a reaction in the presence of a zirconia-supported molybdenum- and potassium-based catalyst,
b) the carbonyl sulphide obtained in step a) undergoes a hydrogenation reaction in the presence of said hydrogen ($H_2$), to form methyl mercaptan ($CH_3SH$) and hydrogen sulphide ($H_2S$),
c) optionally, said hydrogen sulphide ($H_2S$) formed in step b) is recycled to step a), and
d) the methyl mercaptan is collected.

Thus, more particularly, the present invention relates to a process for preparing methyl mercaptan, said process comprising at least the following steps:
a) a carbon oxide, hydrogen sulphide ($H_2S$) and hydrogen ($H_2$) undergo a reaction in the presence of a zirconia-supported molybdenum- and potassium-based catalyst, said catalyst not comprising a promoter, to form carbonyl sulphide,
b) the carbonyl sulphide obtained in step a) undergoes a hydrogenation reaction in the presence of said hydrogen ($H_2$), to form methyl mercaptan ($CH_3SH$) and hydrogen sulphide ($H_2S$), said hydrogen sulphide originating from the hydrolysis of carbonyl sulphide, this hydrolysis being carried out with the water formed during the hydrogenation of carbonyl sulphide,
c) optionally, said hydrogen sulphide ($H_2S$) formed in step b) is recycled to step a), and
d) the methyl mercaptan is collected.

The process for preparing methyl mercaptan according to the present invention thus comprises placing the carbon oxide, hydrogen sulphide ($H_2S$) and hydrogen ($H_2$) reagents in contact in the presence of a zirconia-supported molybdenum- and potassium-based catalyst, said catalyst not comprising a promoter, optionally recycling said hydrogen sulphide ($H_2S$) and collecting the methyl mercaptan. The placing of said reagents in contact in the presence of said catalyst allows carbonyl sulphide to be formed.

The process of the present invention is carried out using a carbon oxide, hydrogen and hydrogen sulphide. The carbon oxide is chosen from among carbon monoxide (CO) and carbon dioxide ($CO_2$). Preferably, the carbon oxide is carbon monoxide (CO), such that the process of the present invention is preferably carried out using a mixture of carbon monoxide, hydrogen and hydrogen sulphide.

More preferably, the catalyst used in step a) of the process is zirconia-supported potassium tetraoxomolybdate ($K_2MoO_4$). According to a particularly preferred embodiment, the catalyst used in step a) of the process is zirconia-supported potassium tetraoxomolybdate ($K_2MoO_4$), and does not comprise a promoter. According to one embodiment, the catalyst used in step a) of the process is constituted by zirconia-supported potassium tetraoxomolybdate ($K_2MoO_4$). The use of this catalyst more specifically allows a high conversion rate to be obtained for the carbon oxide, and in particular carbon monoxide, in addition to a high yield and a high selectivity to methyl mercaptan.

Moreover, the process according to the invention is simple to implement, has a low ecotoxicity and is cost-effective.

Thus, the active component present in the catalyst according to the invention comprises molybdenum and potassium within the same component.

The active component can be obtained by deposition and calcination of $K_2MoO_4$ or $(NH_4)_2MoO_4$ precursors with added $K_2CO_3$ impregnated separately on the support. Ammonium heptamolybdate can also be used as a reagent in the presence of a potassium salt such as potassium nitrate, potassium carbonate or potash for example.

These compounds are precursors of the molybdenum-, oxygen- and potassium- (Mo—O—K)-based active phases, said active phases being obtained after in situ pretreatment of the precursors by, for example, a procedure consisting of a first step of nitrogen drying, followed by sulphidation with hydrogen sulphide, then a reduction/sulphidation step with a mixture of $H_2/H_2S$.

The catalyst support according to the invention is zirconia of the formula $ZrO_2$. Preferably, the weight ratio of the catalyst to zirconia $K_2MoO_4/ZrO_2$ is comprised between 1% and 50%, preferably from 1 to 30%, more preferably between 5 and 35%, such as between 5% to 25%.

The catalytic activity of the catalyst that is of use for the process of the present invention can be further improved when the support of the catalyst has a specific surface area greater than 30 $m^2.g^{-1}$. Preferably, the support material has a specific surface area of at least 50 $m^2.g^{-1}$.

The structure of the support can be a three-dimensional structure that is spherical or cylindrical in shape, ring-shaped, star-shaped or in the form of pellets or any other three-dimensional shape, or in the form of a powder which can be pressed, extruded or pelleted, in a three-dimensional shape.

According to one embodiment, the process according to the invention is a process comprising two consecutive reaction steps (steps a) and b) above), without the need to carry out intermediate purification between the two steps:

$$\text{Step a): } CO+H_2S \rightarrow COS+H_2 \quad (2)$$

$$\text{Step b): } COS+3H_2 \rightarrow CH_3SH+H_2S \quad (3')$$

Step b) corresponds to the outcome of the following two reactions:

$$COS+3H_2 \rightarrow CH_3SH+H_2O \quad (3)$$

$$COS+H_2O \rightarrow CO_2+H_2S \quad (5)$$

More specifically, the hydrogenation reaction of the carbonyl sulphide obtained in step a) in the presence of said hydrogen ($H_2$), forms methyl mercaptan ($CH_3SH$) and hydrogen sulphide ($H_2S$), said hydrogen sulphide originating from the hydrolysis of carbonyl sulphide producing $H_2S$ and $CO_2$, this hydrolysis being carried out with the water formed during the hydrogenation of carbonyl sulphide (and thus producing $CH_3SH$ and water). According to one embodiment, the catalyst is used in steps a) and b) of the process according to the invention.

The process according to the invention is a process comprising two consecutive reaction steps (steps a) and b) above), without the need to carry out intermediate purification between the two steps. In a diagrammatic manner, when the carbon oxide is carbon monoxide, the first step of the process (step a)) is a reaction, preferably carried out at a high temperature, between carbon monoxide and hydrogen sulphide ($H_2S$) according to the reaction (2) described above:

$$CO+H_2S \rightarrow COS+H_2 \quad (2)$$

In the second step (step b)), the carbonyl sulphide formed in step a) undergoes catalytic hydrogenation partially with the hydrogen also formed in step a), according to the reaction (3) described above:

$$COS + 3H_2 \rightarrow CH_3SH + H_2O \quad (3)$$

In one particularly advantageous embodiment of the present invention, the hydrogen sulphide formed in step b) is recycled in step a). In this embodiment, it is seen that the entirety of the hydrogen sulphide formed can thus be reused in step a), which prevents the need to store said hydrogen sulphide formed.

The carbon oxide, the hydrogen sulphide and the hydrogen are advantageously fed continuously or discontinuously into the one or more reactors in which the process according to the invention is implemented, in particular depending on whether the process is implemented continuously or in "batches". Advantageously, the carbon oxide, the hydrogen sulphide and the hydrogen are in liquid or solid or gaseous form, preferably in gaseous form.

The reaction temperature in step a) is advantageously comprised between 500° C. and 1,300° C., preferably between 700° C. and 1,100° C., more preferably between 800° C. and 1,000° C. For conversion purposes for the lower limit and material stability purposes for the upper limit, a temperature range comprised between 700° C. and 1,100° C. is preferred, preferably comprised between 800° C. and 1,000° C.

Using a catalyst according to the present invention, the reaction temperature in step a) is advantageously comprised between 100° C. and 500° C., preferably between 200° C. and 400° C., more preferably between 250° C. and 350° C.

The reaction in step a) can be carried out indifferently at atmospheric pressure, under a positive pressure or under a negative pressure, a person skilled in the art knowing how to adapt the reaction pressure conditions to the nature of the reagents implemented, the chosen reaction temperatures, the flow circulation velocities and the target conversion ratios and yields.

Generally, step a) can be carried out at a pressure comprised between 50 mbar and 100 bar (i.e. between $5.10^3$ and $1.10^7$ Pa), more preferably between atmospheric pressure and 50 bar (i.e. $5.10^6$ Pa), and advantageously between atmospheric pressure and 15 bar (i.e. $15.10^5$ Pa).

Preferably, the reaction can take place in tubular fixed-bed reactors, multi-tubular reactors, microchannel reactors, catalytic wall reactors or fluidised bed reactors.

The invention also relates to the use of the catalyst as defined above for producing methyl mercaptan from carbon oxide, hydrogen sulphide and hydrogen.

The following examples illustrate the invention, however without limiting the scope as defined by the claims accompanying the description of the present invention.

EXAMPLE 1

Preparation of the zirconia-supported $K_2MoO_4$ catalyst

The catalyst was prepared using the dry impregnation method. For this purpose, a quantity of potassium tetraoxomolybdate ($K_2MoO_4$) was dissolved in water and this solution was then impregnated on the zirconia. The Mo content in the catalyst depends on the solubility of $K_2MoO_4$ and on the pore volume of the support.

EXAMPLE 2

Preparation of the silica-supported $K_2MoO_4$ catalyst

The catalyst was prepared using the dry impregnation method. For this purpose, a quantity of potassium tetraoxomolybdate ($K_2MoO_4$) was dissolved in water and this solution was then impregnated on the silica. The Mo content in the catalyst depends on the solubility of $K_2MoO_4$ and on the pore volume of the support.

EXAMPLE 3

Preparation of the titanium dioxide-supported $K_2MoO_4$ catalyst

The catalyst was prepared using the dry impregnation method. For this purpose, a quantity of potassium tetraoxomolybdate ($K_2MoO_4$) was dissolved in water and this solution was then impregnated on the titanium dioxide. The Mo content in the catalyst depends on the solubility of $K_2MoO_4$ and on the pore volume of the support.

EXAMPLE 4

Preparation of the alumina-supported $K_2MoO_4$ catalyst

The catalyst was prepared using the dry impregnation method. For this purpose, a quantity of potassium tetraoxomolybdate ($K_2MoO_4$) was dissolved in water and this solution was then impregnated on the alumina. The Mo content in the catalyst depends on the solubility of $K_2MoO_4$ and on the pore volume of the support.

EXAMPLE 5

Catalytic Test

Before the test, the catalysts were activated in situ by a procedure consisting of a first step of drying in a nitrogen stream at 250° C., following by sulphidation with $H_2S$ at the same temperature for 1 hour and ending with a reduction/sulphidation step with $H_2/H_2S$ at 350° C. for 1 hour.

The performance of the catalysts is then assessed for the methyl mercaptan production reaction in a fixed-bed reactor with a catalyst volume of 3 mL, a temperature of 320° C., at a pressure of 10 bar (1 Mpa), with a volume composition of $CO/H_2/H_2S$ feed gas equal to 1/2/1 and a GHSV (Gas Hourly Space Velocity) equal to 1333 $h^{-1}$. The reagents and the products are analysed in line by gas chromatography.

The results obtained for these 4 catalysts are grouped together in Table 1. For these 4 tests, the molybdenum content on the support is 8 wt %, i.e. 19.9% in $K_2MoO_4$.

TABLE 1

| Example | Catalyst | CO conversion (%) | Molar selectivity (%) | | | $CH_3SH$ yield capacity (g · h$^{-1}$ · $L_{cat}^{-1}$) |
|---|---|---|---|---|---|---|
| | | | $CH_3SH$ | COS | $CO_2$ | |
| 1 | $K_2MoO_4/ZrO_2$ | 77 | 53 | 1 | 44 | 290 |
| 2 | $K_2MoO_4/SiO_2$ | 45 | 49 | 2 | 48 | 158 |
| 3 | $K_2MoO_4/TiO_2$ | 40 | 50 | 4 | 46 | 141 |
| 4 | $K_2MoO_4/Al_2O_3$ | 55 | 42 | 3 | 47 | 164 |

The results shown in Table 1 above show that the catalyst according to the invention (Example 1) procures a clearly improved conversion of the carbon monoxide and clearly improved yield capacity for $CH_3SH$ compared to the catalysts on supports of the prior art (silica, titanium or alumina, examples 2, 3 and 4).

The catalyst of the invention allows methyl mercaptan to be synthesised from carbon oxide, hydrogen and hydrogen sulphide with improved CO conversion, good selectivity and an increased yield capacity for MeSH, combined with an improved conversion of the COS. These enhanced performance levels are obtained on a simple catalyst, without the use of promoters, such as tellurium oxide, nickel oxide, iron oxide and other promoters, as described in the prior art.

The invention claimed is:

1. A process for preparing methyl mercaptan ($CH_3SH$), comprising:
   a) reacting a carbon oxide, hydrogen sulphide ($H_2S$) and hydrogen ($H_2$) in the presence of a zirconia-supported molybdenum- and potassium containing catalyst, the catalyst not comprising a promoter, to form a carbonyl sulphide;
   b) hydrogenating the carbonyl sulphide obtained in step a) in the presence of the hydrogen, to form methyl mercaptan and hydrogen sulphide;
   c) optionally, recycling the hydrogen sulphide formed in step b) to step a); and
   d) collecting the methyl mercaptan.

2. The process according to claim 1, wherein the zirconia-supported catalyst used in step a) comprises a molybdenum- and potassium containing active phase.

3. The process according to claim 1, wherein the zirconia-supported molybdenum- and potassium-containing catalyst used in step a) is $K_2MoO_4/ZrO_2$.

4. The process according to claim 1, wherein the molybdenum- and potassium-containing catalyst is $K_2MoO_4$, where the catalyst comprises between 1% and 50% by weight, relative to the total weight of the catalyst and the zirconia support.

5. The process according to claim 1, wherein the zirconia catalyst support has a specific surface area greater than 30 $m^2.g^{-1}$.

6. The process according to claim 1, wherein the carbon oxide is carbon monoxide (CO).

7. The process according to claim 1, wherein the hydrogen sulphide formed in step b) is recycled in step a).

8. The process according to claim 1, wherein the reaction temperature in step a) is between 100° C. and 500° C.

* * * * *